US00PP14186P29

(12) United States Plant Patent
Danziger

(10) Patent No.: US PP14,186 P2
(45) Date of Patent: Sep. 30, 2003

(54) CHRYSANTHEMUM PLANT NAMED 'DANCHRYCAP'

(50) Latin Name: *Chrysanthemum morifolium*
Varietal Denomination: 'Danchrycap'

(75) Inventor: Gabriel Danziger, Nir-Zvi (IL)

(73) Assignee: Danziger - "DAN" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 10/120,427

(22) Filed: Apr. 12, 2002

(51) Int. Cl.[7] ..... A01H 5/00
(52) U.S. Cl. ..... Plt./296
(58) Field of Search ..... Plt./296, 286

*Primary Examiner*—Bruce R. Campell
*Assistant Examiner*—June Hwu
(74) *Attorney, Agent, or Firm*—Foley & Lardner

(57) ABSTRACT

A new and distinct Chrysanthemum plant named 'Danchrycap' characterized by having corymb shaped plant with greyed-orange ray florets when fully open, RHS 167-A upper surface and RHS 163-B lower surface, and yellow disc florets when fully open, RHS 9-A upper surface and RHS 9-C lower surface; flowering time 7 weeks; short day plant; and vigorous growth habit.

1 Drawing Sheet

Latin name of the genus and species of the plant claimed: *Chrysanthemum morifolium.*

Variety denomination: 'Danchrycap'; commercially, Chrysanthemum cv. Caprice.

BACKGROUND OF THE INVENTION

The present invention relates to a new and distinct cultivar of Chrysanthemum plant, botanically known as *Chrysanthemum morifolium*, hereinafter referred to by the cultivar name 'Danchrycap'.

The new cultivar originated from a cross made in a controlled breeding program in Moshav Mishmar Hashiva, Israel. The female parent is 'Chfl', an upatented proprietary cultivar of the inventor. The male parent is an unnamed open pollnated cultivar. 'Danchrycap' was discovered and selected by the inventor, Gabriel Danziger, as a flowering plant within the progeny of the stated cross in a controlled environment in Moshav Mishmar Hashiva, Israel.

'Danchrycap' was selected in a cultivated environment in Moshav Mishmar Hashiva, Israel. Asexual reproduction of the new cultivar by stem cutting was first performed in January 1999 in Moshav Mishmar Hashiva, Israel and has demonstrated that the combination of characteristics as herein disclosed for the new cultivar are firmly fixed and retained through successive generations of asexual reproduction.

BRIEF SUMMARY OF THE INVENTION

The following traits have been repeatedly observed and are determined to be basic characteristics of 'Danchrycap' which in combination distinguish this Chrysanthemum as a new and distinct cultivar:

1. erect shaped plant with greyed-orange ray florets when fully open, RHS 167-A upper surface and RHS 163-B lower surface, and yellow disc florets when fully open, RHS 9-A (apex) and RHS 9C (base);
2. flowering time 7 weeks;
3. short day plant; and
4. vigorous growth habit.

'Danchrycap' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Danchrycap' is the cultivar 'Europe' (unpatented).

TABLE 1

| Characteristic | 'Danchrycap' | 'Europe' |
|---|---|---|
| Flower Size | 8 cm | 9 cm |
| Flowering time | 7 weeks | 7.5 weeks |
| Growth Potency | High | Medium–High |

A comparison between 'Danchrypcap' and the female parental plant 'Chfl' is shown in Table 2.

TABLE 2

| Characteristic | 'Danchrycap' | 'Chfl' |
|---|---|---|
| Flower color | Orange | Yellow |
| Flower size | 8 cm | 7 cm |
| Form | Single | Single |
| Flowering time | 7 weeks | 7.5 weeks |

BRIEF DESCRIPTION OF THE DRAWING

The accompanying photographic drawing illustrates the overall appearance of the new Chrysanthemum showing the colors as true as is reasonably possible with color reproductions of this type.

The photograph shows a close-up of the inflorescence and foliage of 'Danchrycap'.

DETAILED BOTANICAL DESCRIPTION

The following observations, measurements and values describe the new cultivar as grown in Moshav Mishmar Hashiva, Israel under conditions which closely approximate those generally used in commercial practice. Irrigate and fertilize on regular basis using moderate regime. Mainly grown in greenhouses, can also be grown outdoors during summer. 'Danchrycap' is sensitive to frost. Color references are made to The Royal Horicultural Society Colour Chart (R.H.S.), except where general colors of ordinary significance are used. Color values were taken under daylight conditions at approximately 12:00 p.m. in Moshav Mishmar Hashiva, Israel. The age of the plant described is 17 weeks from planting.

Propagation: Stem cutting.

Plant:

*General appearance and form.*—Height: 90 cm. Width: 20 cm. Shape: Erect. Flowering response: Short day type. Flowering season: Naturally flowers during winter. Winter hardiness: Hardy in moderate climate. Lastingness of the individual bloom: 3–3.5 weeks. Rooting habit: Adventitious roots from cutting base. Time to initiate roots: 6–7 days. Fragrance: None.

Foliage:

*Overall shape of leaf.*—Pinnatifid.

*Base shape.*—Wedge-shaped.

*Apex shape.*—Rounded.

*Margin.*—Serrate.

*Texture.*—Slightly warty.

*Leaf length.*—13 cm.

*Leaf width.*—5 cm.

*Color of upper surface.*—Mature leaf: Yellow-green 147-A. Immature leaf: Yellow-green 147-A.

*Color of lower surface.*—Mature leaf: Yellow-green 147-B. Immature leaf: Yellow-green 147-B.

*Venation color.*—Upper surface: Yellow-green 147-B. Lower surface: Yellow-green 147-C.

*Petiole.*—Length: 3 cm. Diameter: 6 mm. Color: Yellow-green 146-A.

Inflorescence:

*Form.*—Conical.

*Flowering response.*—Short day.

*Quantity of inflorescences.*—8–9 Flowers.

*Inflorescence bud.*—Height: 1 cm. Diameter: 17 mm. Color: Yellow-green 146-B.

*Inflorescence size.*—Diameter: 8 cm. Depth (height): 18–20 mm. Diameter of disc: 20 mm.

*Ray florets.*—Shape: Oblong. Length: 35–40 mm. Width: 12–15 mm.

*Apex shape.*—Acute. Margin: Entire. Texture: Smooth.

*Number of ray florets per inflorescence.*—40–50. Color when opening: Grayed-orange 167-A.

*Color when fully opened upper surface.*—Grayed-orange 167-A.

*Color when fully opened lower surface.*—Grayed-orange 163-B.

*Disc florets.*—Shape: Bell shaped (campanulate). Length: 4–5 mm. Width: 1 mm. Apex: Toothed. Margin: Entire. Texture: Smooth. Number of disc florets per inflorescence: 200–220. Color when opening: Yellow-green 144-A. Color when fully opened upper surface: Yellow 9-A. Color when fully opened lower surface: Yellow 9-C. Color when fully opened lower surface: Yellow 9-C.

*Phyllaries.*—Average size: 80–90 mm. Color: Gray-orange RHS 147A.

*Stem.*—Average length: 90 cm. Average diameter: 8–10 mm. Color: Yellow-green 146-B. Internode length: 20–25 mm.

*Peduncles.*—Length: 15 cm. Diameter: 3.5–4 mm. Texture: Slightly warty. Color: Yellow-green 146-B.

Reproductive organs:

*Stamen.*—Number: 5 fused as a tube. Color: Yellow 13-A.

*Seeds.*—Width: 0.8–1 mm. Length: 1.5 mm. Shape: Achene. Color: Grayed-green 197-A.

*Fruit.*—Achene. Color: Grayed-green 197-A.

*Anthers.*—Color: Yellow 13-A.

*Pollen.*—Color: Yellow 13-A.

*Stigma.*—Color: Yellow 12-B.

*Ovary.*—Color: Yellow-green 149-D.

Disease resistance: Unknown, no susceptibility was observed under regular growing conditions.

I claim:

1. A new and distinct Chrysanthemum plant named 'Danchrycap', substantially as illustrated and described herein.

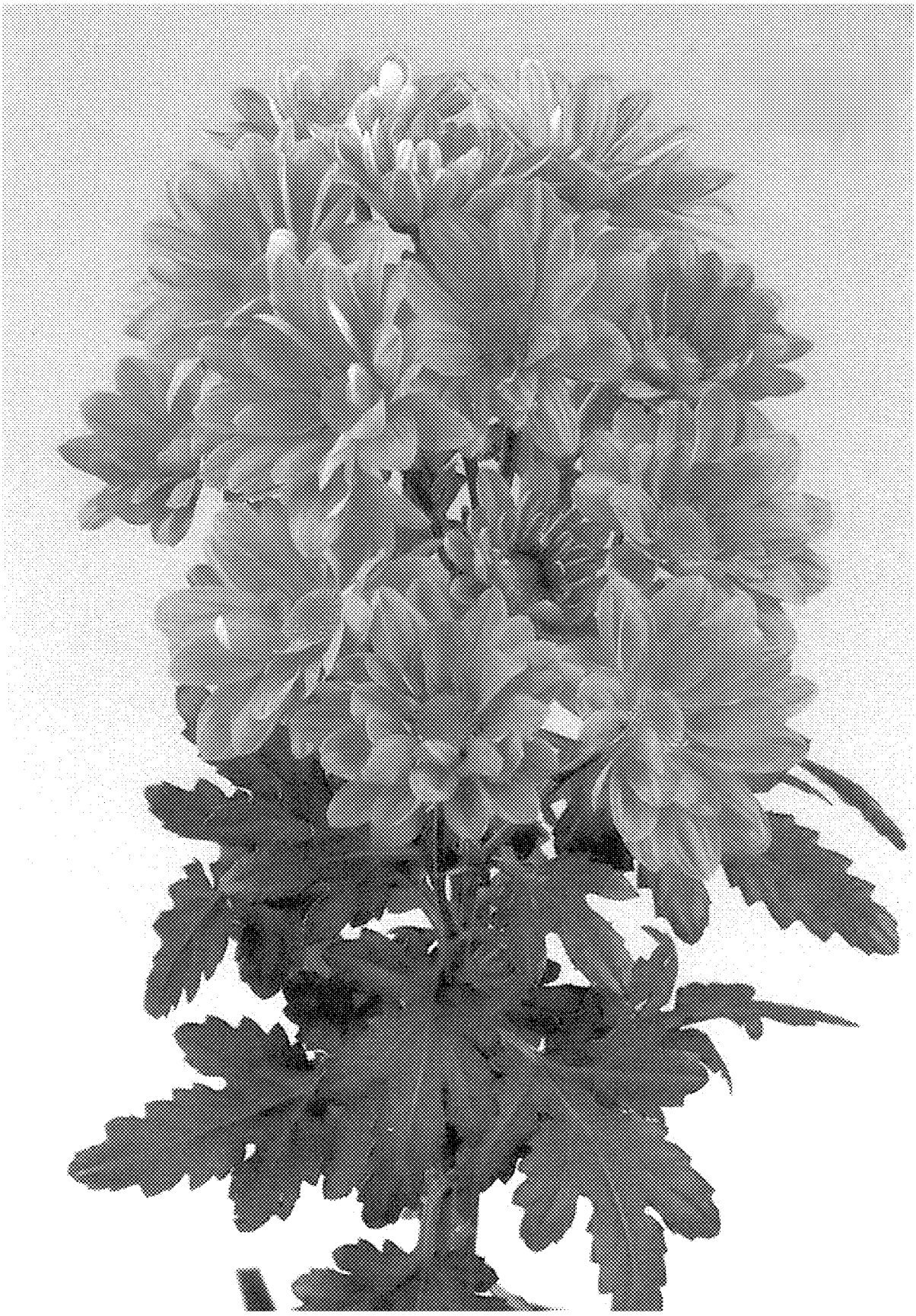

* * * * *